United States Patent [19]
MacCarter et al.

[11] Patent Number: 5,487,753
[45] Date of Patent: Jan. 30, 1996

[54] RATE-RESPONSIVE PACEMAKER WITH ANAEROBIC THRESHOLD ADAPTATION AND METHOD

[75] Inventors: Dean J. MacCarter, Englewood; Don Hopper, Denver; Daniel Cooper, Lakewood; Roger Hassell, Golden, all of Colo.

[73] Assignee: Telectronics Pacing Systems, Inc., Englewood, Colo.

[21] Appl. No.: 405,507

[22] Filed: Mar. 16, 1995

[51] Int. Cl.$^6$ ............................................. A61N 1/365
[52] U.S. Cl. ..................................................... 607/017
[58] Field of Search .................................. 607/17, 18, 19, 607/20, 21, 22, 23, 24

[56] References Cited

U.S. PATENT DOCUMENTS 4,901,725  2/1990  Nappholz et al. .

OTHER PUBLICATIONS

Clinical Experience with an Activity Sensing DDDR Pacemaker Using an Accelerometer Sensor, Chu–Pak Lau, et al. Mar., 1992, PACE, vol. 15, pp. 334–343.
The Range of Sensors and Algorithms Used in Rate Adaptive Cardiac Pacing, Chu–Pak, Lau et al., Aug., 1992, PACE, vol. 15 pp. 1177–1211.

Primary Examiner—William E. Kamm
Assistant Examiner—Scott M. Getzow
Attorney, Agent, or Firm—Gottlieb, Rackman & Reisman

[57] ABSTRACT

A rate responsive pacemaker measures a metabolic demand parameter of a patient. The metabolic demand parameter is converted to a corresponding metabolic indicated rate which determines the pulse rate of the pacer. The converting is based on a profile dependent on the predicted anaerobic threshold level of the patient, as well as his or her age and physical fitness.

27 Claims, 8 Drawing Sheets

RATE-RESPONSIVE PACEMAKER WITH ANAEROBIC THRESHOLD ADAPTATION AND METHOD

BACKGROUND OF THE INVENTION

1. Field of the Invention

This invention relates to rate-responsive pacemakers and, more particularly, to pacemakers that employ a minute volume metabolic demand sensor whose output is adjusted in accordance with a rate response dependent on the anaerobic threshold and physical condition of a patient.

2. Description of the Prior Art

Many attempts have been made to control the heart rate of a pacemaker patient so that it will duplicate the intrinsic heart rate of a healthy person both when the patient is at rest and when the patient is involved in various levels of exercise. Metabolic demand related parameters heretofore proposed for controlling the pacing rate include the QT interval, respiration rate, venous oxygen saturation, stroke volume, venous blood temperature, and minute volume, among others. In addition, the use of mechanical and electrical sensors which detect patient motion have also been explored in such attempts at achieving improved rate-responsiveness. Of the various parameters available, it has been found that pacemakers using minute volume as a parameter for controlling pacing rate are particularly advantageous. However, a problem with these types of pacers has been the mapping of minute ventilation to an appropriate metabolic indicated rate in a manner which accurately reflects the intrinsic heart rate.

A further problem is that, in general, even though metabolically-related parameters used for controlling rate-responsive pacemakers, especially with the contribution of the tidal volume component of minute ventilation, react fairly rapidly to reflect changes in the patient's physical activity, the pacemakers' algorithm does not react with the same speed or time constant. This can result in the patient having a hemodynamic deficiency due to the lag time involved between the start of an increased level of exercise and the reaction thereto by the pacemaker. Of course, since linear mapping is easiest to implement, most mapping attempts so far tended to be straight line approximations, as illustrated in FIGS. 1–5. In FIGS. 1–5, both the vertical and the horizontal scales are normalized for ease of comparison. More specifically, in FIG. 1, the minimum and maximum values of the metabolic rate interval are disposed at 0 and 1 respectfully along the vertical axis. Similarly, corresponding minimum and maximum values of the minute ventilation are disposed at 0 and 1 respectively along the horizontal axis. The same convention is used in FIGS. 2–5 except that in the latter Figures the vertical axis indicates a normalized Metabolic Indicated Rate (MIR) as opposed to an interval.

It should be understood that rate responsive systems making use of the minute ventilation as a parameter, first calculate a long term average for the minute ventilation of a patient and then determine the difference between this long term average and an instantaneous minute ventilation obtained as described below, in conjunction with FIGS. 7–11. The resulting differential parameter is referred to as "the minute ventilation" for the sake of brevity. However, in the drawings, the parameter is identified as ΔMV to indicate that, in fact, this parameter corresponds to the variation of the instantaneous minute ventilation from a long term average value.

Figure 1:
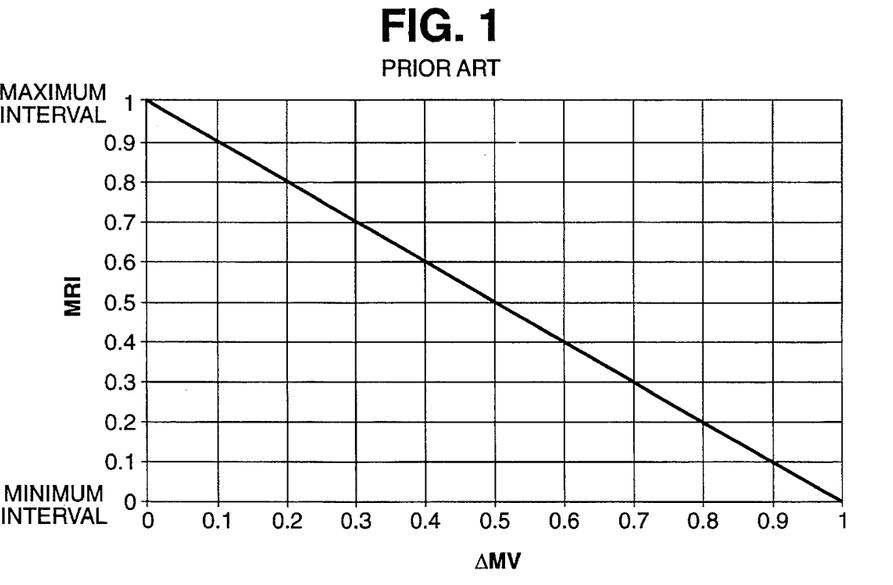
FIGS. 1–5 show various normalized prior art mappings of minute volume to a metabolic indicated rate (MIR) or interval (MRI)
Figure 2:
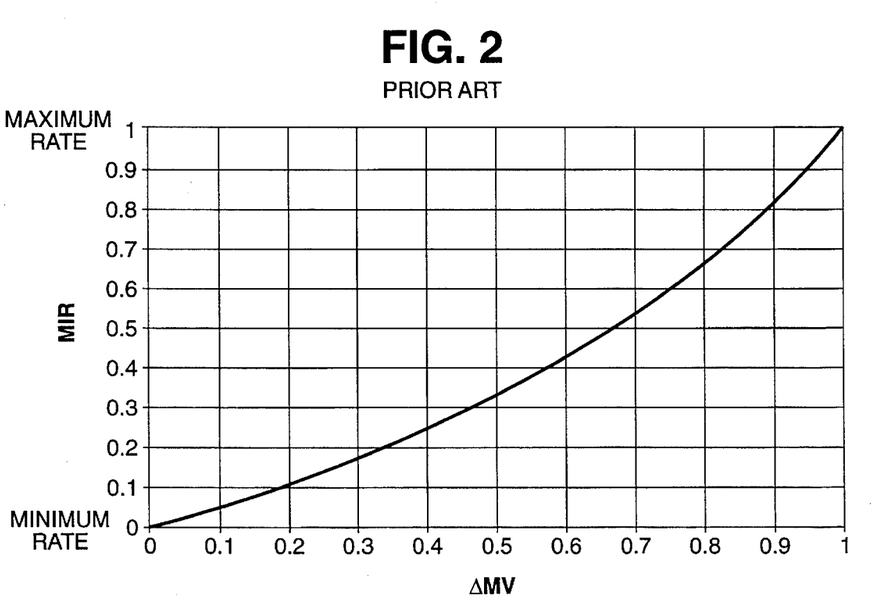

An early attempt at mapping the minute ventilation was to use a straight linear conversion into a pacing interval, or metabolic rate interval (MRI), as shown in FIG. 1. The mapping of FIG. 1 was found to be undesirable because it led to a hyperbolic relationship between the minute ventilation ΔMV and the metabolic indicated rate (MIR), as shown in FIG. 2. This relationship did not reflect the true correlation between the intrinsic heart rate and the minute volume. See "The Range of Sensors and Algorithms used in Rate Adaptive Cardiac Pacing" Chu-Pak Lau, PACE, Vol 15, pg. 1177, August 1992.

Figure 3:
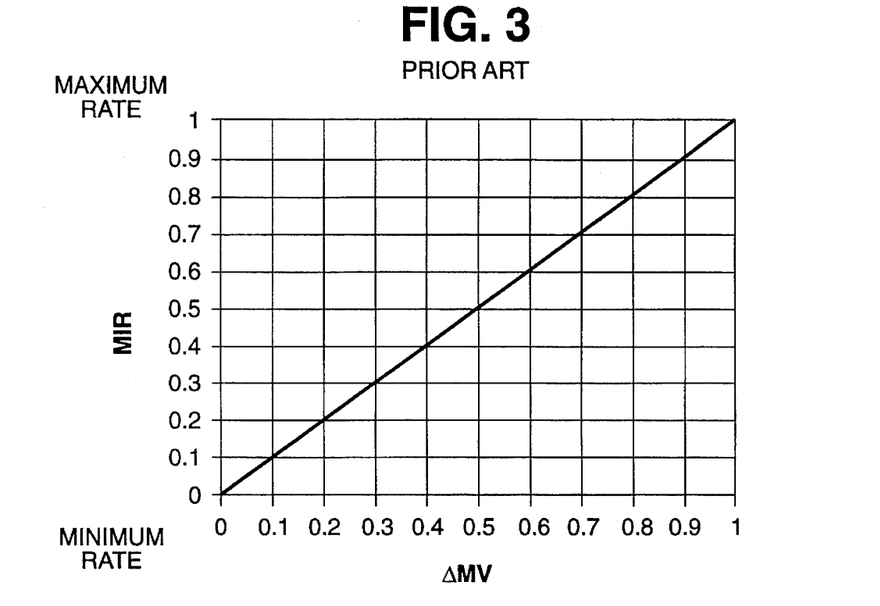

Another type of approach tried in the past was a straight linear correlation between MIR and ΔMV. This method is shown in FIG. 3, and while it conformed more closely to the actual relationship between AMV and the intrinsic heart rate, it was still not satisfactory. More particularly, this straight line approach ignored important factors: first, that initially, at low levels of exercise the relationship between MV and rate is different than at a later stage after the patient has reached anaerobic threshold. Briefly, under anaerobic conditions, a patient's metabolism is operating at a level wherein the oxygen demand exceeds the oxygen intake.

Figure 4:
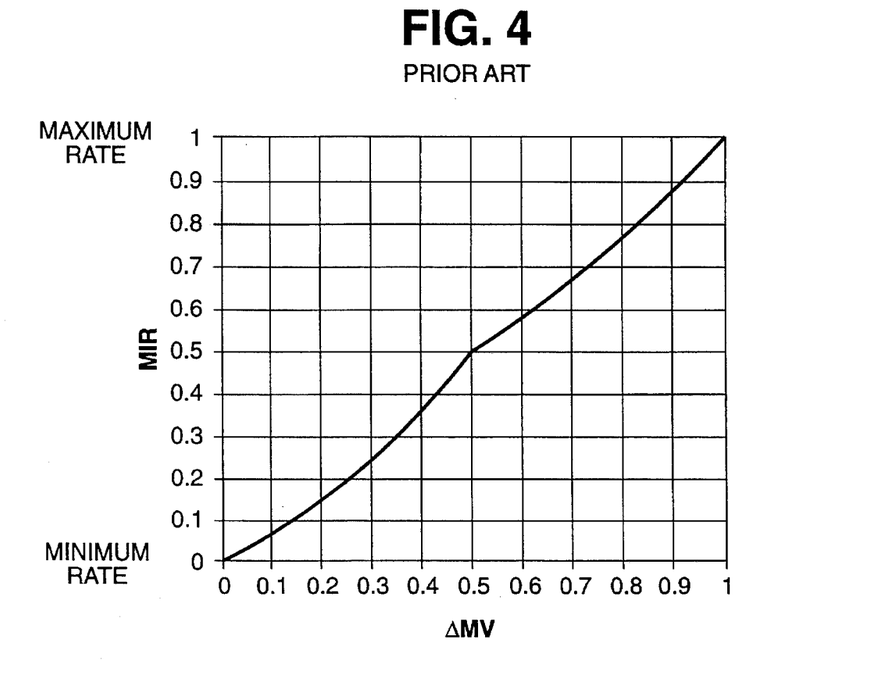

Yet another mapping tried in the past was a two-slope interval-based mapping shown in FIG. 4. This method approximated the real response closely but was still not ideal.

Figure 5:
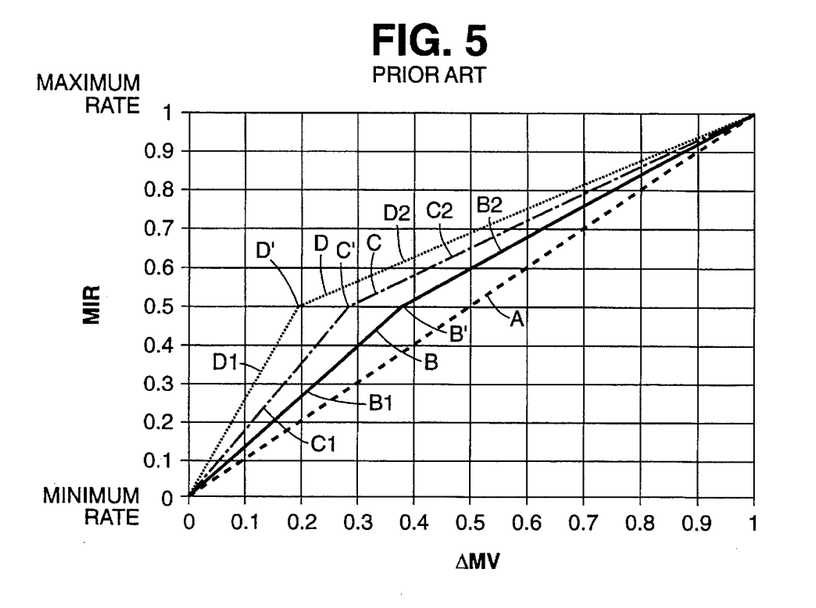

Finally, the mapping, referred to as augmented rate response factor, shown in FIG. 5, was also tried in order to compensate for the slow rate response at low exercise levels. In FIG. 5, line A is the rate response factor (RRF) similar to that of FIG. 3. The rate response factor is a parameter selectable in some pacemakers by a physician based on his evaluation of the patient and his own experience. Profiles B, C and D in this Figure represent three dual slope profiles, each profile consisting of two line segments: an initial, or lower rate segment for the beginning of the exercise having a first slope, and a higher rate segment having a second slope. In order to define the profiles, the physician is given the choice of selecting a low, medium or high initial RRF as the first slope. Each of these initial RRF values is higher than the base RRF. In other words, line segment B1 had a slope equal to a low initial RRF, line segment C1 had a slope equal to a medium initial RRF and line segment O1 had a slope equal to a high initial RRF. In addition to the choice of the initial RRF, the maximum and minimum MIR rates were also left to the physician's discretion or choice based on his experience and physical evaluation of the patient. Next, the break points between the line segments, indicated for each profile as B', C', and D' respectively, was arbitrarily selected at 50% of the maximum MIR, as shown. The second line segment for each profile, i.e., B2, C2, and D2 were then extended from the respective breakpoint B', C', and D' to the upper limit of the base line A, as shown. Even though improved, however, this approach still did not correspond to the actual relationship between the intrinsic heart rate and minute volume, especially at more moderate higher exercise levels. Details of this mapping are described in U.S. Pat. No. 5,292,390 incorporated herein by reference.

In summary, a mapping using a single RRF value as a slope is unsatisfactory because it ignores the need for a faster response during the initial or exercise level, and the need for a decreased response relative to minute ventilation at higher exercise levels. A mapping in which two line segments are used and the initial slope was set to a preselected RRF is still unsatisfactory because it relies on an artificial transition or break point between the line segments.

An ideal solution to the mapping problem would be to set the two slopes independently, as separate variables. However, this approach would be impractical because the transition point between the line segments would be indeterminate and, therefore, may result in responses with either abnormally extended or abnormally contracted initial slopes.

OBJECTIVES AND SUMMARY OF THE INVENTION

In view of the above mentioned disadvantages of the prior art, it is an objective of the present invention to provide a pacemaker which dynamically responds to the instantaneous physical level of activity of a patient and adjusts its pulse rate accordingly, based on a preselected parameter, namely, the ratio of two rate response factors, an initial, and a higher exercise level, rate response factor.

A further objective is to provide a metabolic rate responsive pacemaker which generates pulses at the appropriate rate by following a profile which closely matches the profile of a healthy person, i.e., a person having no pacemaker, both below and above the patient's anaerobic threshold, discussed in more detail below.

Other objectives and advantages of the invention shall become apparent from the following description. Briefly, a pacemaker constructed in accordance with this invention includes sensing means for sensing a metabolic demand parameter of the patient highly correlated or coupled to his or her physical activity. Preferably, the metabolic demand parameter is a minute ventilation, in physiologic terms, which can be determined, for example, from impedance measurements. Minute ventilation has been found to be an accurate representation of the oxygen demand of a patient. This parameter is converted into a corresponding metabolic indicated rate (MIR), whose rate may be used to define the interval between the pacer pulses. The mapping of minute volume to a metabolic indicated rate (MIR), preferably takes into consideration the estimated anaerobic threshold of the patient, his or her age.

The metabolism of a person during exercise can be defined in terms of an aerobic and an anaerobic phase. The aerobic phase corresponds to a sustainable steady state, during which the pulmonary and cardiovascular system provides all the oxygen required by the metabolic demand. In the anaerobic phase, the oxygen demand cannot be met by the system. As a result, in the anaerobic phase, the person can maintain the level of exercise only until oxygen starvation sets in. The transition between these phases is the anaerobic threshold (AT). It has been found experimentally that the AT can be expressed as a heart rate level which is a percentage of the age predicted maximum heart rate of the patient.

In the present invention, if the anaerobic threshold level is between the maximum and minimum heart rate of the patient, a profile formed by two line segments, and having a breakpoint at the anaerobic threshold level, is used for mapping minute volume with a metabolic indicated rate.

As previously mentioned, the ideal solution would be to allow the physician to specify two different rate response factors, each defining the slope of one of the segments. However, this approach is not practical because it may result in one of the segments being too long or too short. The present inventors have found that a well-defined, accurate mapping can be achieved if the physician is allowed to select, instead, the ratio of the rate factors, which corresponds to the ratio of the slopes of the line segments. Allowing the physician to choose the slope ratio provides the physician with a control over both the initial and high level rate response factors. Setting the break point, the heart rate value between the line segments at the AT level, insures that the proper rate response is used for the aerobic and anaerobic metabolic phases, respectively. The slope ratio is selected by the physician dependent on the age of the patient. These two parameters, the anaerobic threshold level and the slope ratio, distinctly define the mapping profile for a patient. The mapping profile is determined while the pacemaker is initialized by the physician.

If the physician so chooses, or if the anaerobic threshold rate is outside a preselected range, instead of the two slope profile, a conventional single line mapping may be used.

DETAILED DESCRIPTION OF THE INVENTION

Figure 6:
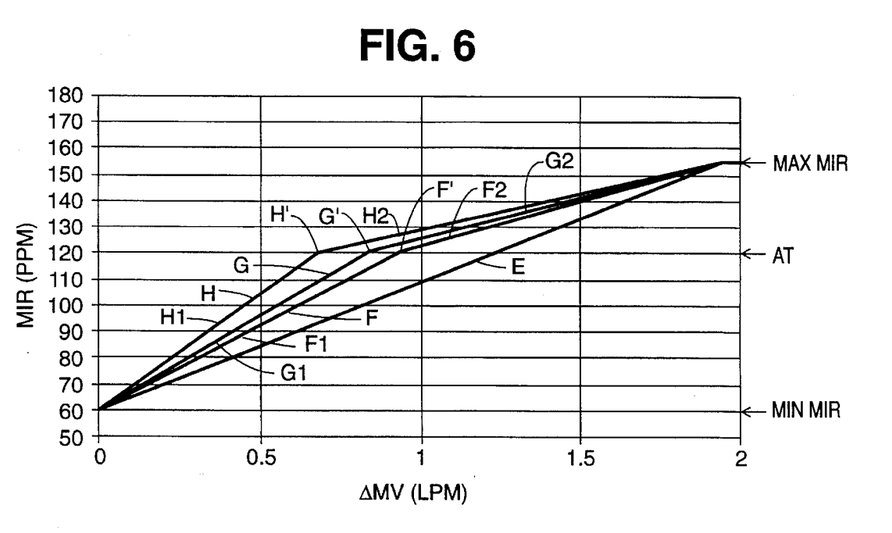
FIG. 6 shows a mapping of the minute volume to the metabolic indicated rate (MIR) in accordance with this invention.

Studies have shown that, while the relationship between the heart rate and the minute volume is complex, it can be modeled fairly accurately by a two-sloped profile having a breakpoint corresponding to the predicted anaerobic threshold level (hereinafter the AT level) of a person. Moreover, the present inventors have further found that the AT level is almost always about 70% of a person's age predicted maximum heart rate (HR), for which there are standard values, while the ratio of the slopes has been found to be related to the age of a person. This AT level was found to be relatively constant for a range of normal subjects with a standard deviation of 8%. A mapping of the relationship of minute volume to MIR, in accordance with this invention, is shown in FIG. 6 for persons of various ages having a selected maximum heart rate of 140 bpm and a normal minimum heart rate of 60 bpm. In FIG. 6, line E characterizes the base rate response factor (RRF) when the anaerobic threshold is not used and profiles F, G and H are used for patients who are of various ages, with 'H' being the youngest. The break points F', G', H' are all positioned at the AT level, which is determined as described above.

Figure 7:
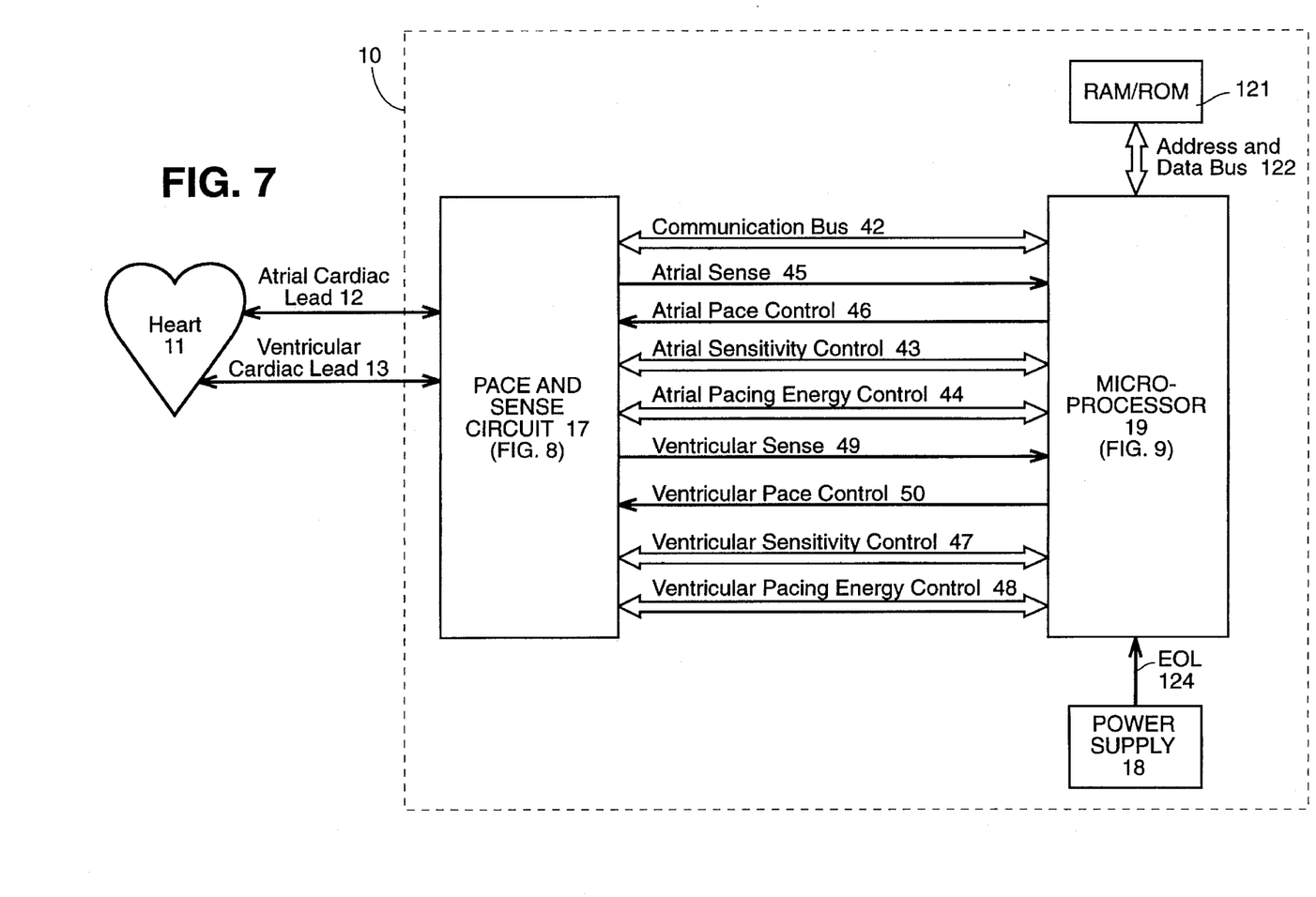
FIG. 7 shows a block diagram of a pacemaker constructed in accordance with this invention.

Details of a pacemaker using the dual slope mapping in accordance with this invention are shown in FIGS. 7–12. FIG. 7 shows a block diagram of the pacemaker. The pacemaker 10 is designed to be implanted in a patient and is connected by leads 12 and 13 to a patient's heart 11 for sensing and pacing the heart 11 as described for example in co-pending application Ser. No. 226,654, filed Apr. 12, 1994 by Tibor A. Nappholz et al., entitled FORCED ATRIOVEN- TRICULAR SYNCHRONY DUAL CHAMBER PACEMAKER, incorporated herein by reference. Briefly, the atrial cardiac lead 12 extends into the atrium of the heart 11 and the ventricular cardiac lead 13 extends into the ventricle of the heart 11. Leads 12 and 13 are used for both sensing electrical activity in the heart and for applying pacing pulses to the heart. The pacemaker 10 includes a pace and sense circuit 17 for the detection of analog signals from leads 12 and 13 and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a voltage supply to the pace and sense circuit 17 and the microprocessor 19 by electrical conductors (not shown). The microprocessor 19 is connected to a random access memory/read only memory unit 121 by an address and data bus 122. A low power signal line 124 is used to provide to the microprocessor 19 a logic signal indicative of a low energy level of the power supply 18. The microprocessor 19 and the pace and sense circuit 17 are connected to each other by a number of data and control lines including a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 8:
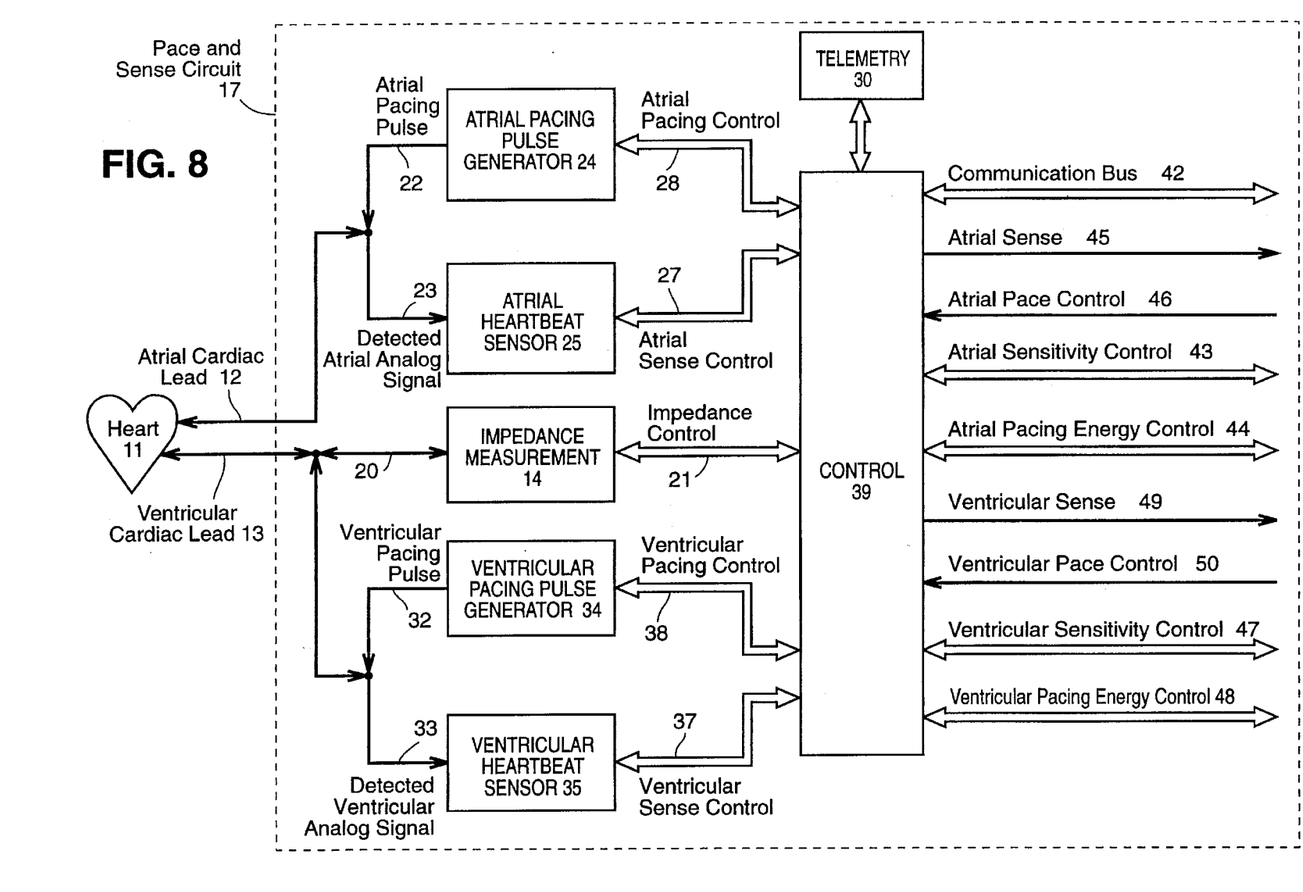
FIG. 8 shows a block diagram of the pace and sense circuit for the pacemaker of FIG. 7.

FIG. 8 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand. The pace and sense circuit 17 also includes a control block 39 which is interfaced to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal on a control bus 27 and an input ventricular sense control signal on a control bus 37, respectively, from the control block 39. These control signals are used to set the sensitivity of the respective sensors.

The atrial pacing pulse generator circuit 34 receives from the control block 39, via an atrial pacing control bus 28, an atrial pace control signal and an atrial pacing energy control signal to generate an atrial pacing pulse 22 at appropriate times. Similarly, the ventricular pacing pulse generator circuit 34 receives from the control block 39, via a ventricular pacing control bus 38, a ventricular pace control signal and a ventricular pacing energy control signal to generate a ventricular pacing pulse 32. The atrial and ventricular pace control signal determine the respective timing of atrial and ventricular pacing that take place, while the atrial and ventricular pacing energy control inputs determine the respective magnitudes of the pulse energies.

The pacemaker 10 performs an impedance measurement when the microprocessor 19 sends a signal on the impedance control bus 21 to activate the impedance measurement circuit 14. The impedance measurement circuit 14 then applies a current to the ventricular cardiac lead 13 via lead 20 and measures a voltage resulting from the applied current. These current and voltage signals define an impedance characteristic of the patient's metabolic demand, and more particularly, of the instantaneous minute volume. This instantaneous minute volume is then filtered and further modified by subtracting from it a long term average value, as discussed above. The resulting parameter is the minute volume parameter.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colo., U.S.A.

Figure 9:
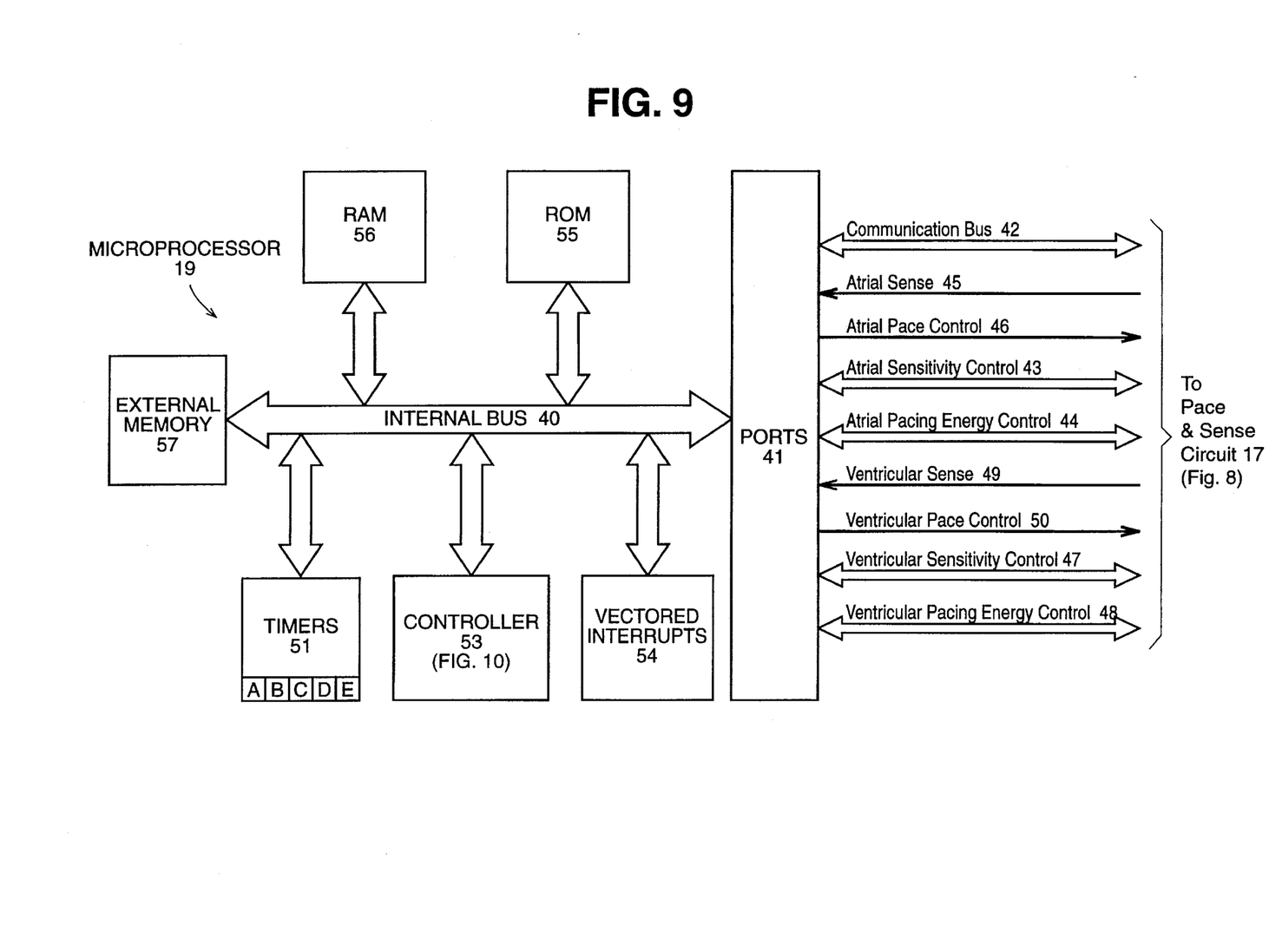
FIG. 9 shows a block diagram of a microprocessor for the pacemaker of FIG. 7.

FIG. 9 shows the microprocessor 19 having a timer circuit 51 for generating several timing signals on its output ports A–E, a controller 53, an interrupt circuit 54, a ROM 55, a RAM 56, an external memory 57 and an interface port 41. Signals between these elements are exchanged via an internal communications bus 40. Timer circuits generate various timing signals at its output ports A–E. The RAM 56 acts as a scratchpad and active memory during execution of the programs stored in the ROM 55 and used by the microprocessor 19. ROM 55 is used to store programs including system supervisory programs, detection algorithms for detecting and confirming arrhythmias, and programming for determining the rate of the pacer, as well as storage programs for storing, in external memory 57, data concerning the functioning of the pulse generator 10 and the electrogram provided by the ventricular cardiac lead 13. The timer circuit 51, and its associated control software, implements timing functions required by the microprocessor 19 without resorting entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 serves to provide signals indicative of such control to the microprocessor 19.

The microprocessor 19 through its port 41 receives the status and/or control inputs from the pace and sense circuit 17, including the sense signals on the sense lines 45 and 49 previously described. Using controller 53, it performs various operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits. The rate of the atrial and/or ventricle pacing is adjusted by controller 53 as set forth below by making use of the anaerobic threshold.

The pacemaker 10 of the present invention will function properly using any metabolic indicator rate system, so long as that system is able to reliably relate the sensed parameter to an appropriate matching of metabolic demand with the paced rate. The preferred embodiment of the invention employs the impedance measurement circuit 14, shown in FIG. 8, which measures the cardiac impedance to determine the respiratory minute volume as described in U.S. Pat. No. 4,901,725 to T. A. Nappholz, et al., issued Feb. 20, 1990 for "Minute Volume Rate-Responsive Pacemaker", incorporated herein by reference.

Figure 10:
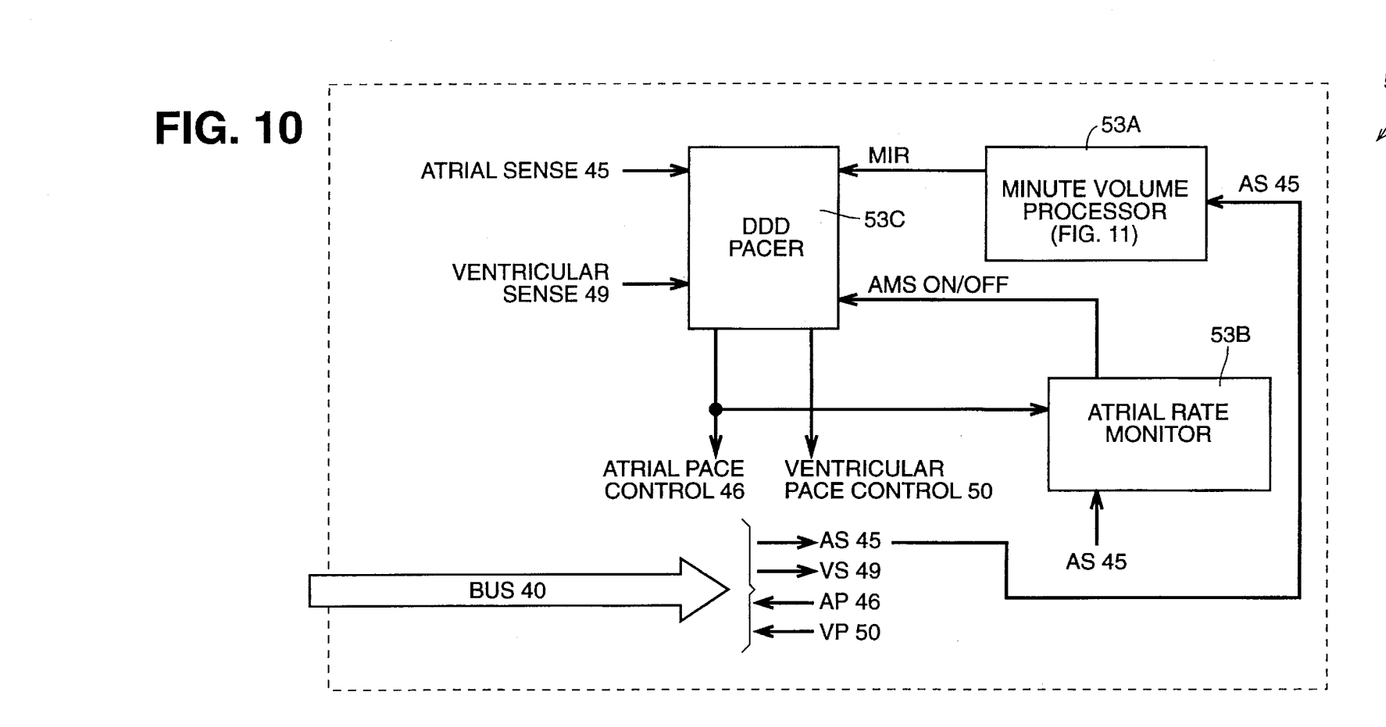
FIG. 10 shows details of the controller for the microprocessor of FIG. 9.

FIG. 10 shows the block diagram of the controller 53 of FIG. 9. The controller 53 includes a pacer 53C, a minute volume processor 53A and an atrial rate monitor 53B. The minute volume processor 53A uses the data supplied via the internal bus 40 and the communication bus 42 from the impedance measurement block 14 to relate the minute volume indicated by the impedance measurement to the Metabolic Indicated Rate (MIR). This rate is then used by the pacer 53C to determine the length of each interval in the timing cycle. While the pacemaker 10 is preferably operating in a DDD mode, it should be understood that it can operate in other modes as well. The atrial rate monitor 53B generates an Automatic Mode Switching (AMS) signal upon detection of a non-physiological atrial rate and rhythm. This AMS signal automatically switches the pacemaker 10 to a ventricular pacing mode, where atrial pacing is temporarily disabled. When a physiological atrial rate resumes, the AMS signal is deactivated and the pacemaker returns to an atrial tracking mode.

Figure 11:
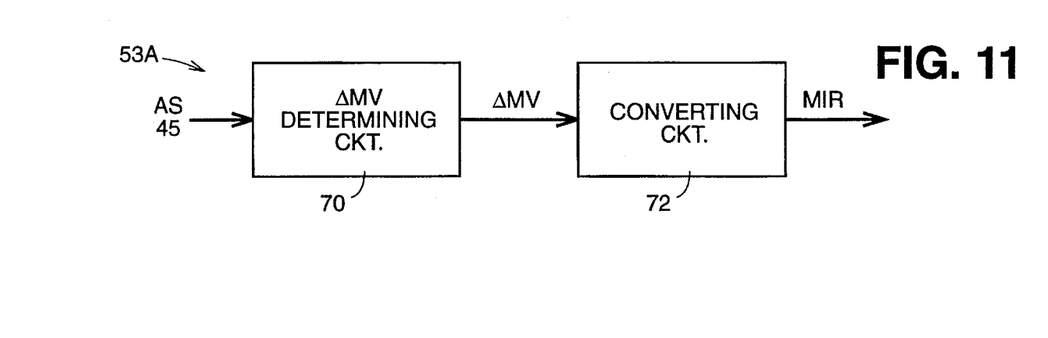
FIG. 11 shows details of the minute volume processor for the controller of FIG. 10.

Referring now to FIG. 11, the minute volume processor 53A includes a minute volume determining circuit 70 and a converting circuit 72. Circuit 70 receives the impedance signal from impedance measurement circuit 14. The corresponding minute volume is determined by circuit 70 as described in detail in the above mentioned U.S. Pat. No. 4,901,725, and is provided to the converting circuit 72. This converting circuit makes use of a mapping profile generated during the initialization of the pacemaker.

It should be understood that while the converting circuit 72 is shown as a discrete element for the sake of clarity, this circuit 72 is preferably implemented by software performed, for example, by microprocessor 39.

Figure 12:
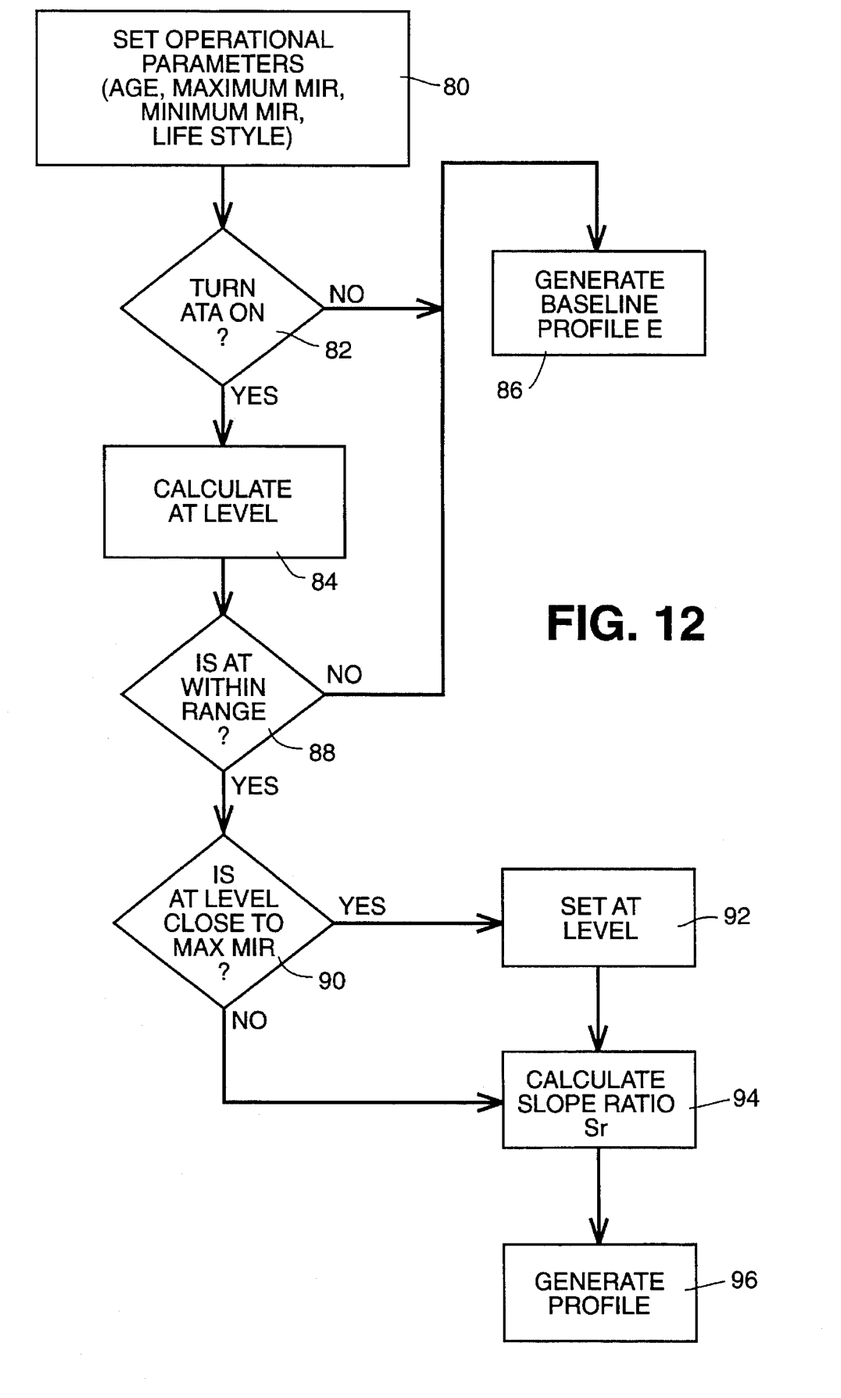
FIG. 12 shows a flow chart describing the operation of the mapping circuit of FIG. 11.

As shown in FIG. 12, during initialization, a plurality of steps are followed to set the profile to be used by the converting circuit 72. These steps include use of an external programmer as discussed above. First, in step 80, the physician sets various operational parameters when the patient is at rest. These parameters include the age of the patient, the maximum MIR rate, and the minimum MIR rate as well as the patient's physical fitness, or life style. Some of these parameters may be preset or calculated by the microprocessor to nominal values and the physician may be given the choice of accepting the nominal value or selecting another value. For example, the maximum MIR rate is normally calculated so that it is equal to 90% of a normal maximum heart rate (HR) based on age. The physician then may decide to accept this nominal value, or may select another value for this parameter. Similarly, the base line RRF may be set for a nominal value of 10. Again, the physician can accept this value, or may decide to set the baseline RRF to a different value.

For example, referring to the profiles of FIG. 6, for a 50 year old patient the normal maximum heart rate (HR) is given by:

$$\text{(1) HR} = 220 - \text{age} = 220 - 50 = 170 \text{ bpm.}$$

This is a standard formula used to determine age predicted maximum HR. The nominal value for the maximum MIR is 90% of maximum HR or about 153 ppm. Thus, in step 80 the maximum MIR rate may be set to 155 ppm, as shown in FIG. 6. Alternatively, the physician may set the maximum MIR to a different value. The minimum MIR is normally set to 60 ppm.

While the present pacemaker has the capability of modifying the MIR mapping based on age and physical fitness, or lifestyle (called herein the Anaerobic Threshold Adapter, or ATA) as described, a physician may decide not to use this feature. Therefore, in step 82, he is given a choice of turning this feature off. If the ATA system is turned off, the mapping is performed in step 86, as described below.

In step 84, the anaerobic threshold (AT) level is calculated. As previously mentioned, it was found that an optimal AT level is given by $$\text{(2) AT} = (\text{HR}) * 0.71$$

For the example of FIG. 6, the AT level is set at about 170×0.71= 120 ppm, as shown in FIG. 6.

In step 88, a decision is made as to whether the AT level is in the range selected in step 80, i.e., whether $$\text{(3) minimum MIR rate} < \text{AT} < \text{maximum MIR rate.}$$

This step is necessary because, while unlikely, it may be possible for the threshold level to fall outside the range of MIR, and the subject pacemaker would be unable to define the breakpoint between the line segments and a corresponding two-slope profile. Therefore, if the calculated AT level is below this range, or if the difference between Max rate and Min rate is less than 10 ppm then circuit 72 generates a straight mapping in step 86. This mapping is defined as the straight line profile E shown in FIG. 6, having a slope equal to RRF (the baseline rate response factor selected or set in step 80). If the AT level is within range, the microprocessor cycles to step 90.

If AT is above Max rate, then the breakpoint is maintained at 10 ppm below Max rate. The lower slope is held fixed and the upper slope is reduced as required.

In step 90, a determination must be made whether the AT level is too close to the maximum MIR rate. If it is too close, for example, within 10 ppm, then the AT level is reset in step 92 to a new value dependent on the maximum MIR rate. For example, the new AT level may be set to be 10 ppm less than the maximum MIR rate.

In step 94, the slope ratio Sr is calculated. As previously mentioned, it was found that the life style of a patient as well as his(her) age determines the slope ratio of the two slope segments used for the mapping. From statistical data, it was determined that the characteristic Sr for the patient varies with age based on a linear regression. More specifically, it was found empirically that for a patient having an average life style or physical condition, the slope ratio is related to age as follows:

$$\text{(4) } Sr_{AVERAGE} = 2.6059 - Age * 0.02047$$

For a sedentary patient, the slope ratio is reduced from the average Sr as follows:

$$\text{(5) } Sr_{SEDENTARY} = (Sr_{AVERAGE} + 1)/2$$

For an athletic patient, the slope ratio is given by:

$$\text{(6) } Sr_{ATHLETIC} = 4.8646 - Age * 0.03356.$$

This expression represents an increase in $Sr_{ATHLETIC}$ of one standard deviation over the slope ratio of equation (4).

In step 94, the slope ratio for the patient is calculated using the above-defined formulas. Alternatively, the slope ratio may be retrieved from a look-up table. A typical look-up table derived from eleven age ranges is shown below, with the actual age used in the formulas being indicated in parentheses.

| AGE | | SEDENTARY | AVERAGE | ATHLETIC |
| --- | --- | --- | --- | --- |
| <25 | (20) | 1.60 | 2.20 | 3.19 |
| 25–34 | (30) | 1.50 | 1.99 | 2.86 |
| 35–44 | (40) | 1.39 | 1.79 | 2.52 |
| 45–54 | (50) | 1.29 | 1.58 | 2.19 |
| 55–64 | (60) | 1.19 | 1.38 | 1.85 |
| 65+ | (70) | 1.09 | 1.17 | 1.52 |

The slope ratio Sr found in step 94 and the anaerobic threshold AT rate from step 90 or 92 are the two parameters which together define the specific dual slope profile (F, G or H) required for mapping by the present ATA system, as shown in FIG. 6.

The profile can be determined by generating the equations for the two line segments from the slope ratio Sr, and the threshold level AT, or by using a look-up table. Thus for a sedentary patient, a profile F is generated having two line segments F1 and F2 (FIG. 6). Similar profiles G and H can be defined for the average and the athletic patient, respectively.

Once the pacemaker 10 is put in operation, the determination circuit 70 periodically measures the minute volume parameter in response to the instantaneous metabolic demand of the patient. The mapping circuit 72 then converts this minute volume into a corresponding MIR using the mapping profile generated as set forth above. For example, for a sedentary 65 year old patient, for every minute volume reading below the AT level, a corresponding MIR is selected by mapping circuit 72 using line segment F1. Above the AT level, an MIR rate is selected using line segment F2. The MIR rate is then fed to the pacer 53C for controlling pacing pulses at the proper rate.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A rate responsive pacemaker comprising:

sensing means for sensing a metabolic demand parameter of a patient;

converting means for converting said metabolic demand parameter into a pulse rate, said converting means receiving said metabolic demand parameter and determining in response thereto a pulse rate in accordance with a preselected function, said function being based on the anaerobic threshold level of said patient; and pulse generating means for generating heart pulses corresponding to said pulse rate.

2. The pacemaker of claim 1 wherein said metabolic demand parameter is related to minute volume.

3. The pacemaker of claim 1 wherein said converting means converts said metabolic demand parameter along one of first and second lines, said first and second lines being joined at a point related to said anaerobic threshold level.

4. The pacemaker of claim 3 wherein said first and second lines have slopes dependent on the physical fitness of said patient.

5. The pacemaker of claim 4 wherein said first and second slopes are defined by a slope ratio, said slope ratio being dependent on the physical fitness of said patient.

6. The pacemaker of claim 1 wherein said anaerobic threshold is related to a maximum nominal rate of said patient.

7. A rate responsive pacemaker for generating heart pulses for a patient, said pacemaker comprising:

sensing means for sensing the minute volume of a patient, said minute volume being related to an instantaneous level of physical activity of said patient;

means for selecting minimum and maximum heart rates for said patient;

means for setting an anaerobic threshold level for said patient based on said heart rates;

profile generating means for generating a profile based on said anaerobic threshold level and the physical fitness of said patient;

converting means for converting said minute volume into a corresponding metabolic indicated rate using said profile; and pulse generating means for generating pulses in response to said metabolic indicated rate.

8. The pacemaker of claim 7 wherein said selecting means is further provided for selecting said physical fitness.

9. The pacemaker of claim 7 wherein said profile includes a first and a second line segment, each line segment having a corresponding slope.

10. The pacemaker of claim 9 wherein said line segments are joined at said anaerobic threshold level.

11. The pacemaker of claim 9 wherein said slopes have a slope ratio based on said physical fitness.

12. The pacemaker of claim 11 wherein said slope ratio is further selected based on the age of said patient.

13. The pacemaker of claim 7 further comprising determining means for determining if said anaerobic threshold level is in a preselected range.

14. The pacemaker of claim 13 wherein said preselected range is defined by said maximum and minimum heart rates.

15. The pacemaker of claim 13 further comprising additional profile mapping means for mapping said minute volume.

16. The pacemaker of claim 15 wherein said additional mapping means is activated when said anaerobic threshold is outside said preselected range.

17. The pacemaker of claim 16 wherein said selecting means is further provided for selectively activating said additional mapping means.

18. The pacemaker of claim 15 wherein said additional mapping means linearly maps said minute volume using a rate response factor.

19. A method of pacing a patient's heart, said patient having an anaerobic threshold heart rate level, said method comprising:

measuring a metabolic demand parameter of said patient, said metabolic demand parameter depending on the instantaneous level of activity of said patient;

converting said metabolic parameter into a metabolic indicated rate using a profile, said profile being dependent on said anaerobic threshold level; and generating heart pulses responsive to said metabolic indicated rate.

20. The method of claim 19 further comprising the step of determining said anaerobic threshold.

21. The method of claim 20 wherein said anaerobic threshold is determined using said patient's age.

22. The method of claim 21 wherein said profile is dependent on the physical fitness of said patient.

23. The method of claim 22 wherein said profile is defined by two line segments.

24. The method of claim 23 wherein said line segments are joined at said anaerobic threshold level.

25. The method of claim 24 wherein said line segments have respective slopes.

26. The method of claim 25 wherein said slopes are defined by a predetermined slope ratio.

27. The method of claim 26 wherein said slope ratio is dependent on said physical fitness and patient age.

* * * * *